United States Patent [19]

Barrett

[11] Patent Number: 4,836,205
[45] Date of Patent: Jun. 6, 1989

[54] GRASPER-STITCHER DEVICE FOR ARTHROSCOPIC ANTERIOR CRUCIATE LIGAMENT REPAIR

[76] Inventor: Gene R. Barrett, Mississippi Sports Medecine and Orthopaedic Center, 1080 River Oaks Office Pl., Jackson, Miss. 39208

[21] Appl. No.: 171,074

[22] Filed: Mar. 21, 1988

[51] Int. Cl.$^4$ .................. A61B 17/04; A61B 17/06; A61B 17/28
[52] U.S. Cl. .................. 128/340; 128/321; 128/335
[58] Field of Search .................. 128/321, 325, 334 R, 128/340, 305, 335; 227/19

[56] References Cited

U.S. PATENT DOCUMENTS 2,751,908  6/1956  Wallace .................. 128/321
2,790,437  4/1957  Moore .................. 128/321

FOREIGN PATENT DOCUMENTS 3601166  7/1987  Fed. Rep. of Germany ...... 128/321

Primary Examiner—Richard C. Pinkham
Assistant Examiner—Gary Jackson
Attorney, Agent, or Firm—Fitzpatrick, Cella Harper & Scinto

[57] ABSTRACT

An elongated grasper-stitcher instrument particularly useful for arthroscopic knee surgery, permits the grasping and stitching of a stump of torn tissue, such as anterior cruciate ligament, or meniscus, during arthroscopic knee surgery. The grasper-stitcher permits multiple loops of suture to engage a stump of tissue at varying levels, and subsequent anchoring of the suture outside of a bore in the lateral pfemoral condyle. The arthroscopic tool defines a pair of atromatic grasping jaws, through parallel fingers of arcuate enclosure, which are spaced laterally so as to accommodate axial passage of a long surgical needle into the proximate end of the elongated tubular housing, through the hollow inner tube, and out through the jaw assembly, even for positions of relative closure between the movable jaw and the fixed jaw. The invention further comprises a method of comparing tissue by permitting several plurality of loops to be defined in the tissue by inserting a first needle with suture through the tissue, and using the opposite end of the suture with a second needle that also is inserted through the hollow tube and out through a receiving cannular, on the opposite side of the tissue through which the loop has been defined.

5 Claims, 4 Drawing Sheets

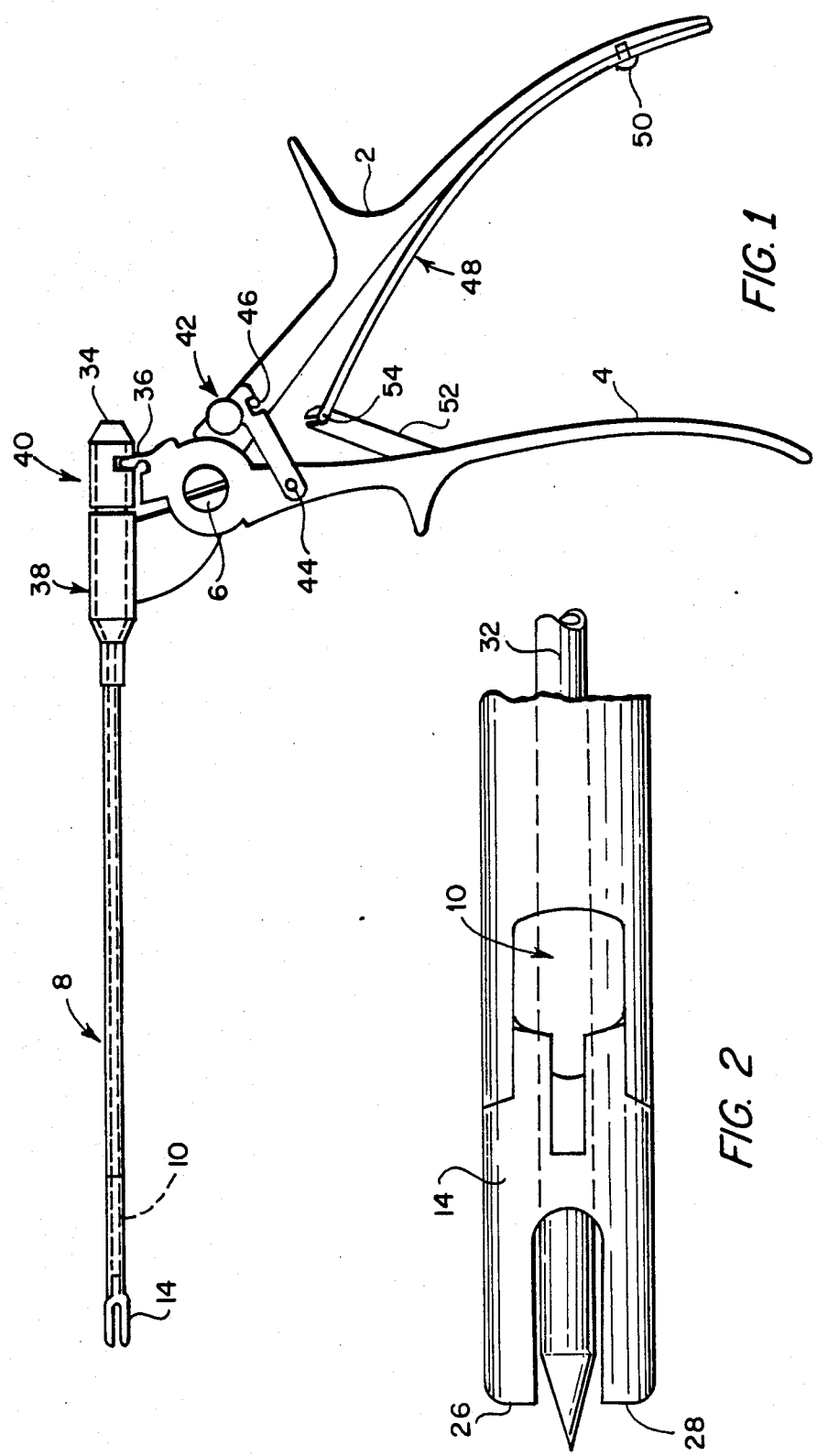

GRASPER-STITCHER DEVICE FOR ARTHROSCOPIC ANTERIOR CRUCIATE LIGAMENT REPAIR

BACKGROUND OF THE INVENTION

1. Field of the Invention

The present invention relates to arthroscopic knee surgery, and specifically to a novel grasper-stitcher device which is intended to facilitate the surgical repair of torn anterior cruciate ligament tissue within the knee cavity. Also disclosed is a method for use of the device.

2. Brief Description of the Prior Art

With the advent of the arthroscope, surgeons have become able to view remotely located areas within the humand body, and therefore operate with fewer incisions, reduced surgical trauma and shorter recovery times.

Recent advantages in arthroscopic knee surgery have focused on the repair of torn meniscal cartilage within the knee cavity. For example, WHIPPLE et al., (U.S. Pat. No. 4,662,371), disclose a cutting-suctioning instrument for removing damaged meniscal cartilage during arthroscopic knee surgery. A pistol grip configuration linearly actuates an inner suction tube that has a distal end connected to a cutting jaw, at one end of an elongated tubular member. The tube serves as a suction passageway for the removal of the cut frgments of tissue. Hence, WHIPPLE et al., addresses rhe problem of remotely cutting damaged cartilage within a knee cavity, and removing fragments with a device that remains in situ for repeated cutting.

MULHOLLAN et al. (U.S. Pat. No. 4,621,640) demonstrate a mechanical needle carrier which can grasp and carry a small, curved surgical needle through a cannula, position the needle and set a stitch through torn meniscal cartilage, then release the needle and be withdrawn from the cannula. However, MULHOLLAN et al. do not address the problem of grasping the free end of acutely injured ligament, peripheral meniscus or even cartilage, to avoid neurovascular damage that might occur when needles are passed blindly, during athroscopic procedures.

STORZ (U.S. Pat. No. 4,607,620) illustrates a medical gripping instrument with an elongated tubular passage and a set of gripping arms, but an instrument configured to simply grasp tissue with the help of an endoscope.

None of these representative prior partents provide a suggestion that a grasper-stitcher as taught herein could be particularly valuable to perform a direct repair, arthrosscopically, by suturing a free end of torn anterior cruciate ligament (ACL) tissue within the knee cavity. Damage to the ACL is a common injury, especially among athletes such as skiers. A problem generally associated with prior art methods for arthroscopic repair of ACL tissue is the difficulty the surgeon encounters in attempting to simultaneously grasp and pass a surgical needle through the torn ACL tissue. A small surgical opening greatly limits his access to the location of the injury. As such, the surgeon is not free to insert one tool to hold and position the damaged tissue, and another to carry out the suturing of the ACL. It would therefore be extremely beneficial to have a surgical instrument which would allow a physician to simultaneously grasp and stitch damaged anterior crucitate ligament tissue within a remotely located knee cavity, under the limitations imposed by arthroscopic surgery.

The prevailing philosophy tody among knee surgeons is that primary repair alone of the anterior cruciate ligament is perhaps less than successful. Repair of a damaged mid substance ACL is still a major problem and has not been successful when done alone. The grasper-stitcher device of the present invention has its primary advantage in permitting a technique for repair of acutely injured ACL that will, it is believed, permit a repair that is sufficiently strong, and simulative of the original action of the ACL, so as to permit augmentation, as by the harvesting of a middle or lateral one-third of patella tendon.

There is definitely a place for arthroscopic repair of the ACL if this repair is backed up by a small extra-articular tenodesis of the iliotibial tract. The repair itself adds stability to the knee as a working unit. In those patients that are perhaps recreational athletes or manual laborers that need to minimize their rehabilitiation time, the present invention offers significant advantage. If the repair of the primary rupture of the ACL can be accomplished arthroscopically without painful arthrotomy incisions, stability is added to the extra-articular augmentation. In the population of 25 to 40 year old recreational athletes or sedentary individuals, an arthroscopic repair of ACL is definitely indicated.

In reviewing the literature there are basically two studies that report "successful" repair of the ACL. A series of articles by Marshall and Warren: Marshall, John L., D.V.M., M.D., F.A.C.S.; Warren, Russell, M.D., F.A.C.S., Wickiewicz, Thomas L., M.D.: Primary Surgical Treatment of Anterior Cruciate Ligament Lesions, The American Journal of Sports Medicine, Vol. 10, No. 2, 1982, 103–107; Warren, Russell F., M.D.: Primary Repair of the Anterior Cruciate Ligament, Clinical Orthopaedics and Related Research, No. 197, Jan–Feb, 1983, pp. 65–70) describe a multiple loop technique. An article by Odenstein, Suture of Fresh Ruptures of the Anterior Cruciate Ligament, ACTA OrthoP. Scand. 55, 270–276, 1984, describes how at least 7 nonabsorbable sutures can be utilized in a repair. Neither one of these techniques had the benefit of an extra-articular stabilizing procedure. The present procedure tends to minimize the stresses on the primary anterior cruciate repair, thus allowing healing to take place. Other studies in the literature, such as those by Feagin and Weaver, describe the use of only several stitches in the repair, but do not describe any type of extra-articular augmentation. According to applicant's procedure, a successful repair preferably comprises six to eight loops of nonabsorbable number 0 suture, and the device of the present invention greatly facilitates such repeated suture steps.

OBJECTS AND SUMMARY OF THE INVENTION

It is accordingly the principal object of this invention to provide a grasper-stitcher instrument for arthroscopic knee surgery, which permits a stump of torn ACL tissue to be simultaneously held and directly stitched.

The above objects are achieved in accordance with the present invention by providing an arthroscopic tool of the general type discussed above with a pair of atraumatic grasping jaws, as well as an elongated tubular member for the passage of long (10–15 inch) surgical needles through a stump of ACL tissue. The grasping jaws are located at one end of the tubular structure, and comprise a moveable first transverse jaw and a stationary, opposed second jaw. Each jaw further comprises a pair of parallel, transversely spaced arcuate finger elements that cooperate to define a longitudinal passage that accomodates passage of a surgical needle in various degrees of relative opening. The moveable first jaw is pivoted about a vertical fulcrum by being connected to the distal end of a hollow tube which is slidable within an elongated, outer tubular housing member. In a preferred embodiment of the invention, a pistol grip configuration is used to linearly actuate this hollow inner tube, and thus control the opening and closing of grasping jaws that are configured especially so as to be atraumatic. A leaf spring is used to urge the jaws into a normally open configuration. An latch with at least one detent is used to position the jaws at a fixed position upon the grasped tissue, once the pistol grip is set at a desired level of compression.

A tubular cannula is used to receive each surgical needle as it is passed through the tissue, being sutured. One receiving cannula type is curved at a radius which matches the back of the knee, in order to be passed over the joint. A second type is straight with a beveled opening, so that it can be passed through a bony canal in the lateral femoral condyle and into a position where its distal end is proximate to the exit point of a needle exiting from its guided passage through ACL tissue or meniscus.

Further objects, features and advantages of the present invention will become more apparent froM consideration of the following detailed description of a preferred embodiment, wherein reference is made to the accompanying drawings.

BRIEF DESCRIPTION OF THE DRAWINGS

FIG. 1 is a left side elevation perspective of a preferred grasper-stitcher device according to the present invention; and, FIG. 2 is an enlarged detail of a left side elevation view of FIG. 1, showing a surgical needle being passed through the jaw assembly; and, FIG. 3 is an enlarged detail top plan view, in partial section, for the jaw assembly of FIG. 2; and, FIG. 4 is a rear elevation view of the device of FIG. 1; and, FIG. 5 is schematic, perspective view showing use of the FIG. 1 device in a first step of a method according to the present invention, wherein a first suture is made in an ACL stump using a firsst needle; and, FIG. 6 is a schematic perspective view showing a second step, wherein the other end of a first suture is passed through the ACL stump with a second needle to create a first loop; and, FIG. 7 is a schematic, perspective view showing a third step, wherein the first end of a second suture is passed through a medially or laterally displaced point of the ACL stump with a third needle; and, FIG. 8 is a schematic, perspective view showing completion of a second loop using the second suture and a fourth needle; and, FIG. 9 is a schematic, perspective view showing the first and second loops completed, will all needles passed through the receiving cannula, and available for anchoring, or further augmentation.

DETAILED DESCRIPTION OF THE PREFERRED EMBODIMENT

Structure of the Device:

A preferred embodiment for a grasper-stitcher made according to the present invention is shown by FIGS. 1-4. With reference to side elevation view FIG. 1, the device comprises a fixed handle, 2, and a movable handle, 4, which are arranged about a pivot, 6. The fixed handle is connected at an upper end to a proximate portion of an elongated, longitudinal outer tubular housing, 8. The movable handle, 4, is positioned to cause longitudinal movement of an elongated hollow inner tube, 10, within the housing, 8, by a connection to a proximate portion of the hollow inner tube, 10.

Figure 3:
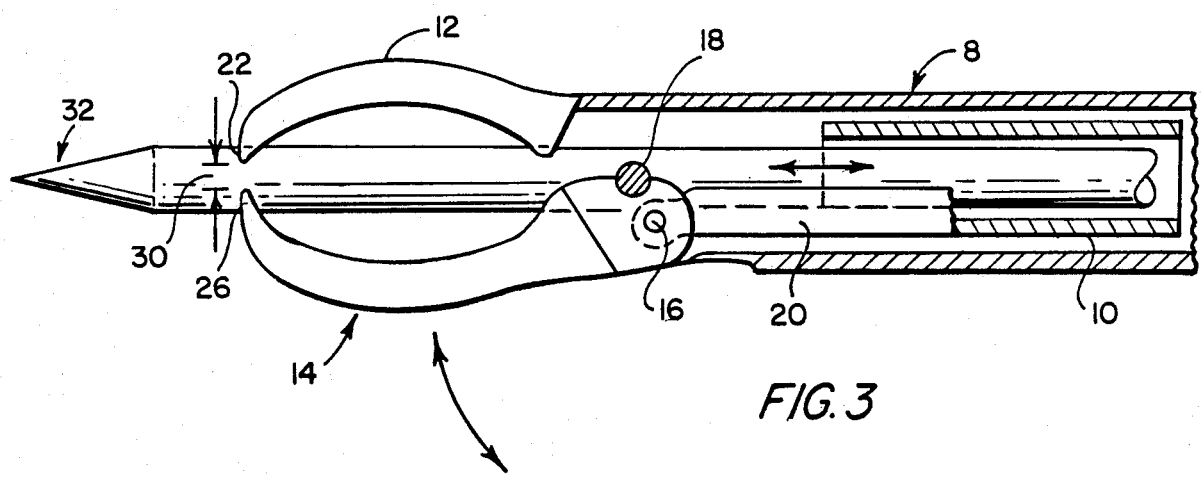

As shown in the detail, partial section side elevation view of FIG. 2, the elongated tubular housing, 8, has a distal end comprising a first movable jaw, 14. Laterally opposed to the first movable jaw, 14, is a second, stationary jaw, 12, shown most clearly by viewing FIGS. 2 and 3. The elongated inner tube, 10, has a flattened distal end extension, 20, that is pinned so as to pivot the movable jaw laterally upon a longitudinal motion within the elongated housing, 8. As shown in FIGS. 2 and 3, the distal end extension of the inner tube, 10, is pinned at 16 so as to cause lateral motion of the movable jaw, 14, about a fulcrum, 18. The extended section, 20, is hollow and connected to the pin, 16, so as not to impede axial or longitudinal insertion of a surgical needle, 32, for purposes which now will be described. The fulcrum, 18, may comprise a pair of pins in opposed side walls of housing, 8, so as not to interfere with an open central space within both the hollow tube, 10, and the jaw assembly region. FIGS. 2 and 3 show two positions as the distal end of the surgical needle, 32, passes through the jaw assembly, and particularly between the claw-like fingers which are spaced to be parallel to the longitudinal axial of the tubular housing, 8.

As shown at FIG. 2, the movable jaw, 14, has a first curved finger-like element, 26, and a second finger-like element, 28, which are longitudinally parallel and laterally spaced apart to facilitate passage of a surgical needle, 32. As further shown in the top, partial section view of FIG. 3, the stationary jaw, 12, has a complementary upper finger, 22. A lower stationary finger, 24 (not shown) is equivalent and opposed to the lower movable finger, 28. In FIG. 3, the jaws are in a relatively closed position, and there is still a clearance space, 30, between a directly opposed tip, (22, 26, and 24, 28) of the fixed and movable jaws. The lateral curvature of both fixed jaw, 12, and movable jaw, 14, cooperates with the clearance space, 30, to create atraumatic engagement of tissue. Tissue trapped between the jaws will tend to slide along the arcuate inner surfaces towards the larger central zone, if completely encircled. If a stump or mass of tissue is not completely encircled, then the non-closure of opposed tips, (22, 26, and 24, 28) as by space 30, helps to ensure that the surgeon will not unduly apply compression to the tissue, and cause trauma. FIG. 2 shows that lateral spacing between upper and lower arcuate fingers, 24, 26, of each jaw will facilitate clearance of axially disposed surgical needle, 32.

Figure 4:
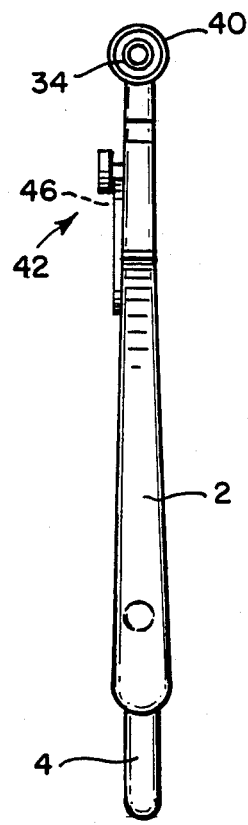

A preferred technique to axially translate the hollow inner tube, 10, with respect to the tubular housing, 8, is provided by a rear connector, 40, which is fixed to the hollow inner tube, 10, as shown in FIGS. 1 and 4. The fixed handle, 2, is welded or otherwise connected to a cannister-like rear support, 38, which in turn is welded or otherwise secured to the elongated hollow housing, 8. Upon closure of the movable handle, 4, towards the fixed handle, 2, movable jaw, 14, is urged into the closed position, of FIG. 3. This action is result of counterdockwise rotation of the handle, 4, and contact of pin, 36, in a vertical slot within the rear connector, 40. The rear connector, 40, as well as the rear support, 38, are hollow tubular members and, as shown in FIG. 4, there is a guided entraceway, 34, at the proximate end of the device that enables a surgical needle, 32, to be axially inserted, enter through the hollow supports, 38, 40, and then be guided along the longitudinal extent of the hollow inner tube, 10. In FIG. 2, the distal end of a needle, 32, is just proximate the distal end of the jaw assembly, and in FIG. 3, the distal end has passed through the jaw assembly, even through the movable jaw, 14, is in its relatively closed position. Clearance for the needle, 32, primarily is provided by the lateral spacing between each of the fingers, (26, 28, and 22, 24) which comprise the movable jaw and fixed jaws, respectively.

In order to control the compression force being exerted at the jaw assembly, a leaf spring element, 48, is pinned at a proximate end, 50, and a distal end is connected into a notch, 54, at the distal end of a spring support, 52, that in turn is attached to the movable handle, 4. In this fashion, the spring will tend to force the jaws into a normally open position, and the surgeon will have jaw closure pressure resisted by action of the spring. Further, a latch, 42, may have detent, and be pinned as at 44, so as to permit fixing of the instrument at a desired amount of relative compression, through tightening of a screw member, 46. A ratchet type of latch also may be employed. The latch allows the surgeon to fix the amount of compression exerted by the jaws with respect to grasped tissue, and thereafter concentrate on insertion of needles through the entrance, 34, along the hollow tubular member, 10, and outwardly through the jaw assembly, 14.

Use of the device of FIGS. 1-4, will become more apparent with reference to the schematic procedural steps shown in FIGS. 5-9, inclusive.

Method for Use of the Device:

Utilizing 10 inch double needles with number 0 nonabsorbable suture, applicant hereafter teaches a novel technique for repair of the ACL. If some ligament tissue can be gotten back to the isometric femoral drill hole then it is felt to be repairable, and the technique is attempted. Preferably, 6 to 8 sutures are distributed throughout the anterior cruciate stump, thus distributing the stresses throughout the already plastically deformed structure. The stitches at the base of the anterior cruciate stump on the tibia also snug the synovial sleeve up around the anterior cruciate stump, thereby enhancing blood supply to the region and healing. The ligament stump is brought into a drill hole in bone, thus allowing good fixation and enhancement of blood supply. By passing the sutures through the ligament in an oblique fashion, as will be described, more of the ligament stump is traverse with each pass. The sutures thereby tend to align with individual fibers comprising the ACL.

The preferred extra-articular procedure utilizes one free strip of iliotibial tract that goes beneath the fibular collateral ligament. This keeps the iliotibial tract behind the center of rotation of the knee, thus preventing the problem known as pivot shift phenomenon. A second layer of posterior iliotibial tract also may be secured with a screw to help prevent the pivot shift phenomenon. Free ends of the the strips can be passed under the fibular collateral ligament. It is preferred to use number 5, nonabsorbable suture in the extra-articular procedure, to create a double layer of "synthetic" extra-articular ligament. The position of the extra-articular procedure is optimized by putting the screw directly at Krackow's point with a cancellous screw and toothed washer. The isometricity of both the intra-articular repair and the extra-articular augmentation are checked on the operating table by taking the knee through a full range of motion. The screw fixation also allows immediate motion in a CPM machine and subsequent passive extension during the first week of postoperative treatment.

In the case of mid substance ACL tears, especially in young athletic individuals, a patella tendon intra-articular augmentation may be utilized. Preferrably, repairing the anterior cruciate stump around the patella tendon graft is accomplished with a double needle, multiple loop technique. This enhances blood supply from the ligament stump on the tibial end. In a situation where there is a young, athletic individual with associated pathology such as meniscus tears, the use of the patella tendon augmentaation is more aggressively applied. From a review of such patients, the "isolated" anterior cruciate tears do quite well with an intra-articular, double needle, multiple loop repair technique. Patients that require patella tendon augmentation tend to have more associated pathology and also are more competitive individuals.

In summary, the double needle multiple loop anterior cruciate ligament repair technique with extra-articular augmentation appears to be a viable alternative in the slightly older individuals, and those that are recreational athletes. In a test of this technique, several competitive athletes also did well. This technique allows easier and quicker rehabilitation without compromise of extensor mechanism. In those individuals that have associated pathology, are more competitive athletically and are of a younger age, the patella tendon augmentation has proved helpful. However, even in these patients the anterior cruciate stump preferrably should be repaired around the patella tendon, utilizing the double needle multiple loop technique. Although the results are preliminary, the following technique appears viable, easily accomplished and worthwhile when arthroscopic technique is called for.

SURGICAL TECHNIQUE EXAMPLES

1. ACL repair.

A thorough examination under anesthesia is first done on both knees in order to compare laxity in both knees an to define instability of the affected knee. The leg is then placed in a leg holder that includes a tourniquet, thereby allowing placement on the proximal thigh. This allows flexion past 90 degrees for proximal exposure. The knee and leg from the tourniquet to the toe are then prepped for 10 full minutes with Betadine and then double draped. A diagnostic anthroscopy is begun by inserting a large bore (7 mm.) inflow cannula into the superior medial portal. Meniscal repair or partial excision is performed, as necessary. Number 0 nonabsorbable suture is used to allow immediate postoperative passive motion.

Any debris including excess fat pad or hypertrophic synovium is removed from the intracondylar notch and the existing anterior cruciate stump is retracted medially. A large burr is then introduced into the anterior medial portal and a lateral notch plasty is accomplished. The notch is widened from anterior opening to the posterior intercondylar shelf, where the remaining anterior cruciate fibers can be identified.

Figure 5:
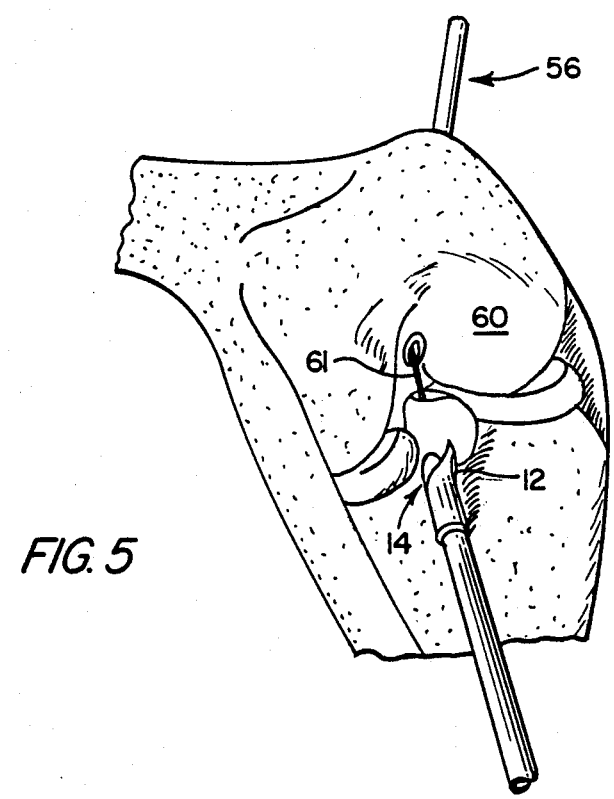

As shown in FIG. 5, a small drill hole approximately 4.5 mm. is made through a puncture hole in the anterior medial tibial flare. The hole is made through the medial tibial condyle, 60, exiting just anterior to the ACL stump, 58. With the knee flexed 90-100 degrees a guide pin is driven from inside out, through the lateral femoral condyle. This pin is then over reamed with a 6 mm. reamer. A large bore cannula is then placed through the femoral drill hole and into the intracondylar notch behind the ACL stump.

Figure 6:
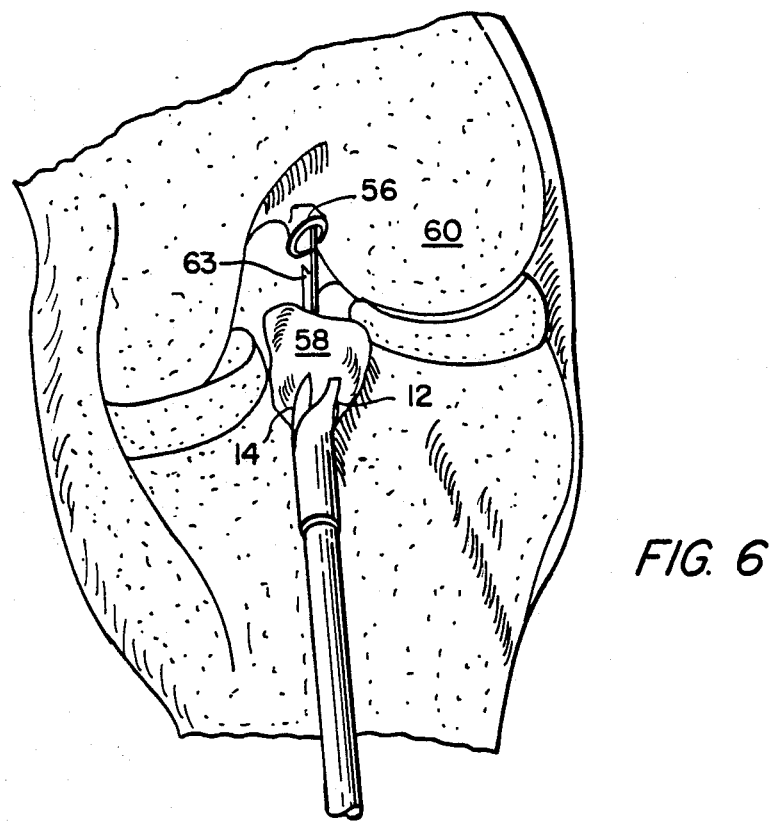

As shown in FIGS. 5, 6, a small receiving cannula, 56, is passed through the tibial drill hole. The ACL stump, 58, is then grasped with the grasper-stitcher jaws 12, 14, as described hereinbefore, through the anterior medial portal and actually folded back over the cannula through the tibia. Using 10 inch double needles 61, 63, and at least a number 0 nonabsorbable suture, a loop is passed through the ACL stump, 58, from the tibial cannula through the stump and through the femoral cannula, and exits laterally. A first loop is shown being formed between entrance points 62, 64, by use of two needles, 61, 63, attached at opposite ends of a first suture, in FIG. 7.

Figure 7:
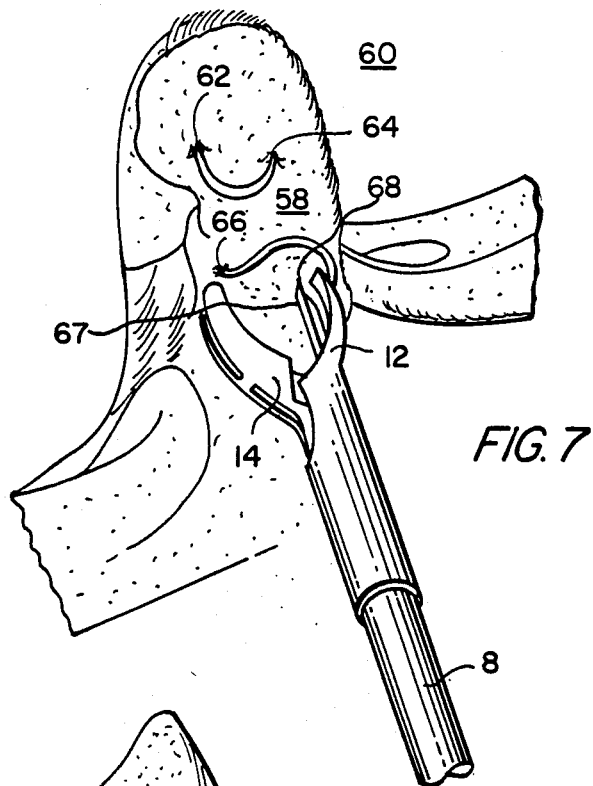
Figure 8:
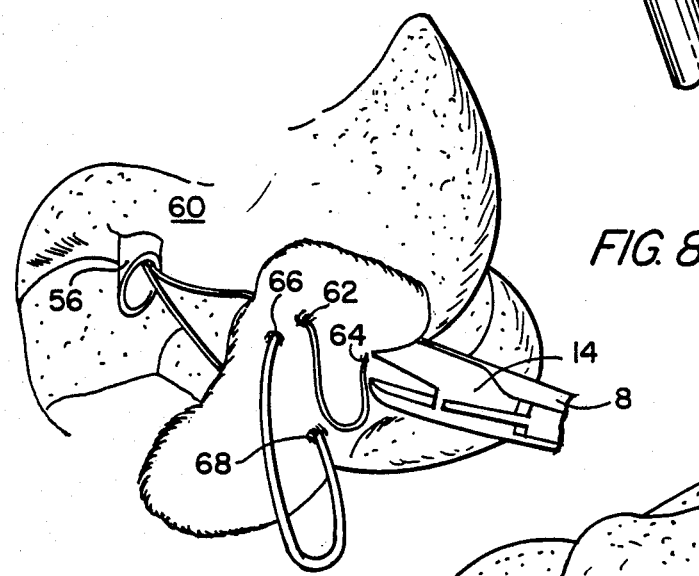
Figure 9:
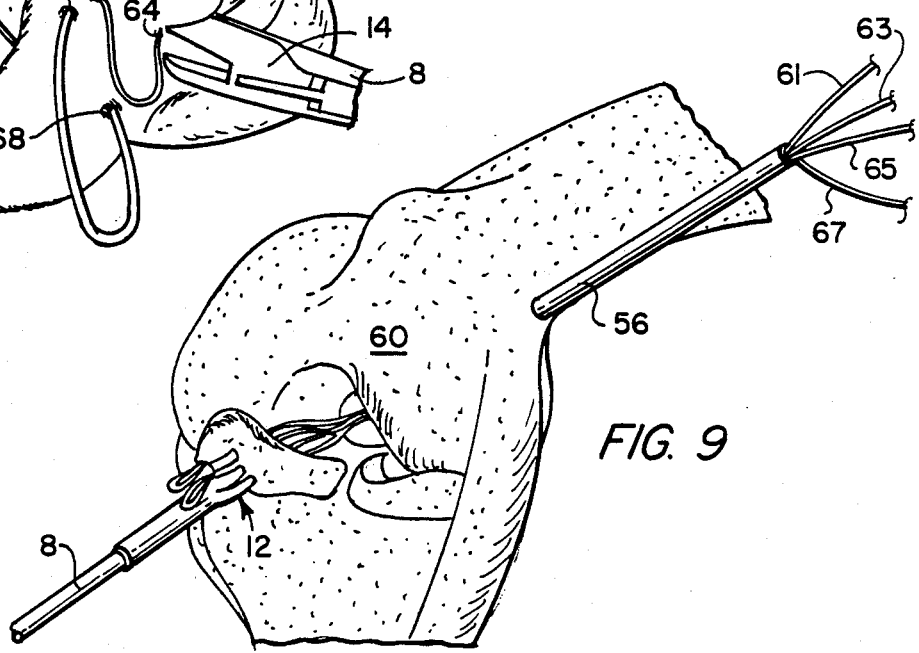

As shown by FIGS. 7 and 8, the ACL stump, 58, further is manipulated by selective actions of the jaws of the grasper-stitcher, in order to obtain different positions for the second, and each following, suture loop. A second set of needles 65, 67, attached to opposite end of a second suture creates a second loop between points, 66, 68. At least six to eight loops of number 0 nonabsorbable suture preferrably are passed through the ACL stump and out the lateral side. As shown in FIG. 9, all such loops then can all be pulled tightly through grasping of the set of needles (61, 63, 65, 67) that were passed through the receiving cannula, 56, thereby allowing the tension to be dispersed throughout the ACL stump as the ACL is being pulled into the femoral drill hole. The free ends of the loops then are tied around a screw (not shown) that also may be utilized in the lateral augmentation procedure, discussed hereafter.

2. Lateral augmentation.

If a mid substance tear is identified in the ACL, a middle or lateral one-third of the patella may be utilized for intra-articular augmentation. The small puncture hole in the anterior medial tibial flare area is expanded to approximately a 1-2 inch incision. The middle or lateral one-third of the patella tendon is harvested with a ½ inch × ¼ inch plug of bone off the tibia. Three drill holes are placed in this plug of bone prior to removal.

The patella tendon is then dissected off the patella without harvesting a large petalla bone plug. A number 5 permanent stitch is woven through the holes in the tibial bone plug and through the proximal free end of the patella tendon. Two sutures are placed in each end. The hole in the tibial flare is then expanded to approximately an 8 mm. hole. A suture passer is then passed through the lateral femoral condyle, through the intracondylar notch and out the titial hole. A number 20 wire that has been twisted into a loop may be used for this step. The patella tendon is then pulled retrograde through the tibia hole, through the ACL stump and out the femoral hole. The bony plug from the tibia rests in the tibial hole. A small staple is then utilized to secure this bony plug in the oblique tibial hole. The sutures are tied around the staple. The sutures in the proximal end are tied around the same screw that the ACL stump sutures have been repaired around. Even though the ACL is mid-substance, a multi-loop repair is accomplished in the stump in addition to the intra-articular patella tendon augmentation.

3. Extra-articular procedure.

The posterior border of the iliotibial tract is identified, and an incision is made 1.5 cm. anterior to the posterior border. One centimeter anterior to that incision a second incision is made creating a free iliotibial tract slip. A number 5 suture permanent stitch is placed in both strips. The free iliotibial tract slip is then passed under the fibular collateral ligament from anterior to posterior. The septum is actually taken off the femur right at the point recommended by Krackow, et al. and using a 3.2 mm. drill bit a hole is made in this area for the screw. A depth guage is then used to determine the exact length of the screw and approximately 5 mm. is added to the measured length. A Polyethylene washer backed by a steel washer is then placed on the screw and it is passed through the posterior band. The number 5 suture is then tied around the screw. The free strip is then passed under and around the screw, and the screw is then secured. The sutures from the intra-articular procedure to repair the ACL tear are wrapped around the same screw. Hemovacs are then inserted into the intracondylar area and the lateral incision, and then closure is accomplished in a routine fashion.

Postop procedure is that the patient is placed in a hinged brace locked at 45 degrees. On the second day postop, constant passive motion is begun from 40-60 degrees, for slowly increasing the flexion. Daily the brace is removed and passive extension is obtained to at least 10 degrees.

In summary, and as illustrated schematically by the surgical steps of FIGS. 5-9, use of the grasper-stitcher has made the intra-articular aspect of the ACL repair much easier. By inserting the device through the anterior medial portal, the stump of an ACL can be securely grasped and manipulated without damage to the ligament tissue. Rather than having to separately secure the ACL stub while passing the 10 inch needles through a tibial drill hole, these long needles are passed directly through the instrument of the present invention. As each needle is passed through the ACL stump, the needle safely enters a separate receiving cannula, that is positioned against movement within the bored hole in the lateral femoral condyle.

While I have described a preferred embodiment of my invention, it is to be understood that the invention is to be limited solely by the scope of the appended claims.

I claim:

1. A grasper-stitcher device adapted to grasp tissue, and permit passage of sutures through the grasped tissue comprising, in combination:

a longitudinal, elongated housing, having a proximate end connected to a handle means and a distal end comprising a jaw assembly means;

an inner hollow tubular member capable of axial motion within the elongated housing assembly, with a proximate end attached to said handle means, and a distal end connected to a proximate end of at least one movable first jaw member of said jaw assembly means at the distal end of the tubular housing;

said jaw assembly means further comprising said movable first jaw member laterally opposed from a fixed second jaw member, wherein each jaw member further comprises a pair of arcuate finger-like elements that are laterally spaced and parallel to a longitudinal axis of the housing, distal ends of each jaw member laterally are spaced apart when said first jaw member is in a relatively closed position, and an axially open passage is provided between an entrance at the proximate end of the elongated housing through the hollow inner tubular member and out through the arcuate jaw members at the distal end of the housing, even when said jaw members are in a relatively closed position, whereby a long surgical needle may be inserted into the proximate end of the housing, pass through the hollow inner tubular member and exit through the jaw assembly means and suture a tissue grasped within said jaw assembly.

2. A grasper-stitcher according to claim 1, wherein said handle means comprises a fixed handle that is fixed at one end to a housing which supports the proximate end of said elongated housing, and a movable handle that is pinned to said fixed handle and includes a distal end that engages with a rear connector member connected to said inner hollow tubular member, whereby closure of said handles will cause longitudinal motion of said inner hollow tubular member towards the distal end of the elongated housing, and a closure of said movable jaw member towards said fixed jaw member.

3. A grasper-stitcher according to claim 2, wherein said jaw assembly further comprises said movable jaw member being pinned to an extending distal portion of said inner hollow tubular member, wherein said extended portion is curved and pinned to a proximate portion of the movable jaw member, and a pin fulcrum is located between the connection with the movable hollow tubular member and the distal end of the movable jaw member.

4. A grasper-stitcher according to claim 3, wherein the movable jaw member and the fixed jaw member each are arcuate, and have inner opposed surfaces that remain laterally separated by a distance greater than the distance between the distal ends of the jaw members, when said movable jaw member is moved into a closed position, with respect to the fixed jaw member.

5. A grasper-stitcher according to claim 4, wherein the movable jaw member is urged into a normally open position by said handle means which further comprises a spring to urge the movable handle away from the fixed handle, and said handle means further comprises a latch that is pivoted so as to fix the relative position between the handles to ensure a desired compressive action at the jaw assembly.

* * * * *